(12) United States Patent
Defossa et al.

(10) Patent No.: US 8,148,375 B2
(45) Date of Patent: Apr. 3, 2012

(54) (CYCLOPROPYLPHENYL) PHENYLOXAMIDES, METHOD FOR THE PRODUCTION THEREOF, AND USE OF SAME AS A MEDICAMENT

(75) Inventors: Elisabeth Defossa, Idstein (DE); Thomas Klabunde, Frankfurt (DE); Viktoria Dietrich, Frankfurt (DE); Siegfried Stengelin, Eppstein (DE); Guido Haschke, Wetzlar (DE); Andreas Herling, Bad Camberg (DE); Johanna Kuhlmann-Gottke, Frankfurt (DE); Stefan Bartoschek, Frankfurt (DE)

(73) Assignee: Sanofi-Aventis, Paris (FR)

( * ) Notice: Subject to any disclaimer, the term of this patent is extended or adjusted under 35 U.S.C. 154(b) by 11 days.

(21) Appl. No.: 12/724,517

(22) Filed: Mar. 16, 2010

(65) Prior Publication Data
US 2010/0261644 A1    Oct. 14, 2010

Related U.S. Application Data

(63) Continuation of application No. PCT/EP2008/007217, filed on Sep. 4, 2008.

(30) Foreign Application Priority Data

Sep. 21, 2007   (EP) ..................... 07291131

(51) Int. Cl.
*A61K 31/53* (2006.01)
*A61K 36/328* (2006.01)
(52) U.S. Cl. ...................... 514/243; 424/748
(58) Field of Classification Search .......... None
See application file for complete search history.

(56) References Cited

U.S. PATENT DOCUMENTS

| 6,890,568 B2 * | 5/2005 | Pierce et al. ................. 424/729 |
| 2003/0092702 A1 | 5/2003 | Cirillo et al. |
| 2005/0124667 A1 | 6/2005 | Sartori et al. |

OTHER PUBLICATIONS

Lindenmayer, Jean-Pierre, Treatment of Refractory Schizophrenia.*
Azzouz, Mioun, Gene Therapy for ALS: Progress and Prospects, Biochemica et Biophysica Acta 1762 1122-1127 (2006).*
Citron, Martin Alzheimer's diasease: treatments in discovery and development, Nature Nueroscience Supplement, vol. 5, 1055-1057, Nov. 2002.*
Korczyn and Mussbaum, Emerging Therapies in the Pharmacological Treatment of Parkinson's Disease, Drugs, (62) 775-766, (2002).*
Margolis, Russell. Diagnosis of Huntington's Disease, Clinical Chemistry (49:10) 1726-1732 (2003).*
Martin, Lee. Nuerodegeneration in exitotoxicity, global cerebral ischemia, and target deprivation: A perspective on the contributions of aptosis and necrosis, Brain Research Bulletin, vol. 46, No. 4, 281-309 (1998).*
Mattson, Mark P. Pathways Towards and Away from Alzheimer's Disease, Nature, vol. 430, 631-639, (2004).*
Patel, ShirishV. pharmacotherapy of Cognitive Impairment in Alzheimer's Disease: A Review. Journal of Geriatric Psychiatry and Neurology, vol. 8 81-95 (1995).*

* cited by examiner

*Primary Examiner* — Anish Gupta
*Assistant Examiner* — Jeanette Lieb
(74) *Attorney, Agent, or Firm* — Jiang Lin; Scully, Scott, Murphy & Presser, P.C.

(57) ABSTRACT

The invention relates to (cyclopropylphenyl) phenyloxamides and their physiologically tolerated salts, and their use as a medicament.

12 Claims, No Drawings

(CYCLOPROPYLPHENYL)PHENYLOXAMIDES, METHOD FOR THE PRODUCTION THEREOF, AND USE OF SAME AS A MEDICAMENT

This application is a Continuation of International Application No. PCT/EP2008/007217, filed Sep. 4, 2008, which is incorporated herein by reference in its entirety.

The invention relates to (cyclopropylphenyl)phenyloxamides and their physiologically tolerated salts.

Compounds of similar structure have been described in the prior art (see US2005/0124667), as well as the use thereof as antithrombotics.

The invention was based on the object of providing compounds which display a therapeutically useful effect. The object was in particular to find novel compounds suitable for the treatment of hyperglycemia and diabetes.

The invention therefore relates to compounds of the formula I

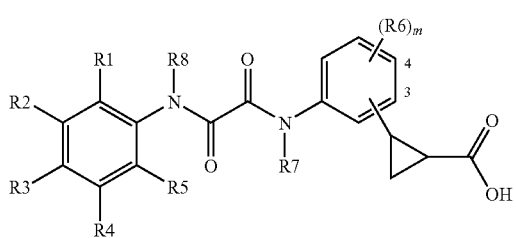

in which the meanings are

R1, R2, R3, R4, R5 independently of one another H, F, Cl, Br, CN, $CF_3$, OH, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn, $SO_2$—$(C_1-C_4)$-alkyl, $SO_3H$, $SO_2NR9R10$, NR9R10 or $SO_2$—N-piperidinyl, where alkyl and phenyl may be substituted one or more times by R12;

R7, R8 independently of one another H or $(C_1-C_6)$-alkyl;

m 0, 1, 2, 3 or 4;

R6 OH, F, Cl, Br, CN, $OCH_3$, $OCF_3$, $CH_3$, $CF_3$, $(C_1-C_6)$-alkyl or O—$(C_1-C_6)$-alkyl, where alkyl may be substituted one or more times by OH, F, Cl, Br or CN;

R9, R10 independently of one another H, $(C_1-C_6)$-alkyl or phenyl, where alkyl may be substituted one or more times by F, Cl or Br, and phenyl may be substituted one or more times by R6;

R11 F, Cl, Br, CN, OH, O—$(C_1-C_6)$-alkyl, $(C_1-C_6)$-alkyl, $(C_2-C_6)$-alkenyl, $(C_2-C_6)$-alkynyl or NR9R10;

R12 F, Cl, Br, CN, OH, O—$(C_1-C_6)$-alkyl, $(C_1-C_6)$-alkyl, $(C_2-C_6)$-alkenyl, $(C_2-C_6)$-alkynyl, NR9R10, COOH, COO—$(C_1-C_4)$-alkyl, $SCH_3$, $SCF_3$, $SO_2$—$(C_1-C_4)$-alkyl, $SO_3H$ or $SO_2NR9R10$;

and the physiologically tolerated salts thereof.

Preference is given to compounds of the formula I in which one or more radicals have the following meanings:

R1, R2, R3, R4, R5 independently of one another H, F, Cl, Br, CN, $CF_3$, OH, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn, $SO_2$-$(C_1-C_4)$-alkyl, $SO_3H$, $SO_2NR9R10$, NR9R10 or $SO_2$-N-piperidinyl, where alkyl and phenyl may be substituted one or more times by R12;

R7, R8 H;

m 0, 1, 2, 3 or 4;

R6 OH, F, Cl, Br, CN, $OCH_3$, $OCF_3$, $CH_3$, $CF_3$, $(C_1-C_6)$-alkyl or O—$(C_1-C_6)$-alkyl, where alkyl may be substituted one or more times by OH, F, Cl, Br or CN;

R9, R10 independently of one another H, $(C_1-C_6)$-alkyl or phenyl, where alkyl may be substituted one or more times by F, Cl or Br, and phenyl may be substituted one or more times by R6;

R11 F, Cl, Br, CN, OH, O—$(C_1-C_6)$-alkyl, $(C_1-C_6)$-alkyl, $(C_2-C_6)$-alkenyl, $(C_2-C_6)$-alkynyl or NR9R10;

R12 F, Cl, Br, CN, OH, O—$(C_1-C_6)$-alkyl, $(C_1-C_6)$-alkyl, $(C_2-C_6)$-alkenyl, $(C_2-C_6)$-alkynyl, NR9R10, COOH, COO—$(C_1-C_4)$-alkyl, $SCH_3$, $SCF_3$, $SO_2$—$(C_1-C_4)$-alkyl, $SO_3H$ or $SO_2NR9R10$;

and the physiologically tolerated salts thereof.

Particular preference is given to compounds of the formula I in which one or more radicals have the following meanings:

R1 H, F, Cl, Br, CN, $CF_3$, OH, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl R2 H, F, Cl, Br, CN, $CF_3$, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn;

R3 H, F, Cl, Br, CN, $CF_3$, OH, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn;

R4 H, F, Cl, Br, CN, $CF_3$, OH, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn;

R5 H, F, Cl, Br, CN, $CF_3$, OH, $OCF_3$, $OCHF_2$, $SCH_3$, $SCF_3$, phenyl, Ophenyl, COOH, COO—$(C_1-C_6)$-alkyl, CO—$(C_1-C_6)$-alkyl, $(C_1-C_6)$-alkyl, O—$(C_1-C_6)$-alkyl, OBn;

where at least one of the radicals R1 to R5 has a meaning other than hydrogen;

R7, R8 independently of one another H or $(C_1-C_6)$-alkyl;

m 0;

R9, R10 independently of one another H or $(C_1-C_6)$-alkyl, where alkyl may be substituted one or more times by F, Cl or Br;

and the physiologically tolerated salts thereof.

If radicals or substituents can occur more than once in the compounds of the formulae I, they may all have the stated meaning independently of one another and be identical or different.

The alkyl, alkenyl and alkynyl radicals in the radicals R1, R2, R3, R4, R5, R6, R7, R8, R9, R10, R11 and R12 may be either straight-chain or branched.

The invention relates to compounds of the formula I in the form of their salts, racemates, racemic mixtures and pure enantiomers, and their diastereomers and mixtures thereof.

The invention further relates both to mixtures of stereoisomers of the formula I and to the pure stereoisomers of the formula I, and to mixtures of diastereomers of the formula I and to the pure diastereomers. The mixtures are separated for example by chromatographic means.

The present invention includes all possible tautomeric forms of the compounds of the formula I.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as, hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts and solvates as described herein.

An alkyl radical means a straight-chain or branched hydrocarbon chain such as, for example, methyl, ethyl, isopropyl, tert-butyl, hexyl. The alkyl radicals may be substituted one or more times as described above.

The invention also includes solvates, hydrates and alcohol adducts of the compounds of the formula I.

The compound(s) of the formula I can also be administered in combination with further active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of body weight, for example 3-10 mg/kg/day. An intravenous dose may be for example in the range from 0.3 mg to 1.0 mg/kg, which can suitably be administered as infusion of from 10 ng to 100 ng per kilogram per minute. Suitable infusion solutions for this purpose may comprise for example from 0.1 ng to 100 mg, typically from 1 ng to 100 mg, per milliliter. Single doses may comprise for example from 1 mg to 10 g of the active ingredient. Thus, ampoules for injections may comprise for example from 1 mg to 100 mg, and single-dose formulations which can be administered orally, such as, for example, tablets or capsules, may comprise for example from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of at least one compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration include preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally comprise from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are:

All antidiabetics which are mentioned in the Rote Liste 2007, chapter 12; all weight-reducing agents/appetite suppressants which are mentioned in the Rote Liste 2007, chapter 1; all lipid-lowering agents which are mentioned in the Rote Liste 2007, chapter 58. They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, LANTUS® (see www.lantus.com) or HMR 1964 or LEVEMIR® (insulin detemir) or those described in WO2005005477 (Novo Nordisk), fast-acting insulins (see U.S. Pat. No. 6,221,633), inhalable insulins such as, for example, EXUBERA® or oral insulins such as, for example, IN-105 (NOBEX) or ORAL-LYN™ (Generex Biotechnology), GLP-1-derivatives and GLP-1 agonists such as, for example, exenatide, liraglutide or those which have been disclosed in WO98/08871 or WO2005027978, WO2006037811, WO2006037810 of Novo Nordisk A/S, in WO01/04156 of Zealand or in WO00/34331 of Beaufour-Ipsen, pramlintide acetate (Symlin; Amylin Pharmaceuticals), BIM-51077, PC-DAC:Exendin-4 (an Exendin-4 analog which is covalently bonded to recombinant human albumin), agonists like those described for example in D. Chen et al., Proc. Natl. Acad. Sci. USA 104 (2007) 943, those described in WO2006124529, and orally effective hypoglycemic active ingredients.

Antidiabetics also include agonists of the glucose-dependent insulinotropic polypeptide (GIP) receptor like those described for example in WO2006121860.

The orally effective hypoglycemic active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose 1,6-bisphosphatase
modulators of glucose transporter 4 (GLUT4),
inhibitors of glutamine-fructose-6-phosphate am idotransferase (GFAT),
GLP-1 agonists,
potassium channel openers such as, for example, Pinacidil, Cromakalim, Diazoxide or those described in R. D. Carr et al., Diabetes 52, 2003, 2513,2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 of Novo Nordisk A/S, inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators (retinoid X receptor) and
active ingredients which act on the ATP-dependent potassium channel of the beta cells.

In one embodiment of the invention, the compound of the formula I is administered in combination with an HMGCoA reductase inhibitor (3-hydroxy-3-methylglutaryl coenzyme A) such as simvastatin, fluvastatin, pravastatin, lovastatin, atorvastatin, cerivastatin, rosuvastatin or L-659699

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB), and WO2006017257 (Phenomix) or WO2005033100 (Lipideon Biotechnology AG), or in WO2004097655, WO2004000805, WO2004000804, WO2004000803, WO2002050068, WO2002050060, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163.

In one embodiment of the invention, the compound of the formula I is administered in combination with Vytorin™, a fixed combination of ezetimibe with simvastatin.

In one embodiment of the invention, the compound of the formula I is administered in combination with a fixed combination of ezetimibe with atorvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate with rosuvastatin.

In a further embodiment of the invention, the compound of the formula I is administered in combination with Synordia®, a fixed combination of fenofibrate with metformin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR (peroxisome proliferator activated receptor) gamma agonist such as, for example, rosiglitazone, pioglitazone, JTT-501, GI 262570, R-483, CS-011 (rivoglitazone).

In one embodiment of the invention, the compound, of the formula I is administered in combination with Competact™, a fixed combination of pioglitazone hydrochloride with metformin hydrochloride.

In one embodiment of the invention, the compound of the formula I is administered in combination with Tandemact™, a fixed combination of pioglitazone with glimepride.

In a further embodiment of the invention, the compound of the formula I is administered in combination with a fixed combination of pioglitazone hydrochloride with an angiotensin II agonist such as, for example, TAK-536.

In one embodiment of the invention, the compound of the formula I is administered in combination with a PPAR (peroxisome proliferator activated receptor) alpha agonist such as, for example, GW9578, GW-590735, K-111, LY-674, KRP-101, DRF-10945, LY-518674 or those described in WO2001040207, WO2002096894, WO2005097076.

In one embodiment of the invention, the compound of the formula I is administered in combination with a mixed PPAR (peroxisome proliferator activated receptor) alpha/gamma agonist such as, for example, naveglitazar, LY-510929, ONO-5129, E-3030, AVE 8042, AVE 8134, AVE 0847, CKD-501 (lobeglitazone sulfate) or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR (peroxisome proliferator activated receptor) delta agonist such as, for example, GW-501516 or as are described in WO2006059744, WO2006084176, WO2006029699, WO2007039172-WO2007039178.

In one embodiment, the compound of the formula I is administered in combination with metaglidasen or with MBX-2044 or other partial PPAR (peroxisome proliferator activated receptor) gamma agonists/antagonists.

In one embodiment of the invention, the compound of the formula I is administered in combination with a fibrate such as, for example, fenofibrate, clofibrate, bezafibrate.

In one embodiment of the invention, the compound of the formula I is administered in combination with an MTP inhibitor (microsomal triglyceride transfer protein) such as, for example, implitapide, BMS-201038, R-103757, AS-1552133 or those described in WO2005085226, WO2005121091, WO2006010423.

In one embodiment of the invention, the compound of the formula I is administered in combination with a CETP inhibitor (cholesterol ester transfer protein) such as, for example, torcetrapib or JTT-705 or those described in WO2006002342, WO2006010422, WO2006012093, WO2006073973, WO2006072362, WO2006097169, WO2007041494.

In one embodiment of the invention, the compound of the formula I is administered in combination with a bile acid absorption inhibitor (see, for example, U.S. Pat. No. 6,245, 744, U.S. Pat. No. 6,221,897 or WO00/61568), such as, for example, HMR 1741 or those as described in DE 10 2005 033099.1 and DE 10 2005 033100.9, WO2007009655-56.

In one embodiment of the invention, the compound of the formula I is administered in combination with a polymeric bile acid adsorber such as, for example, cholestyramine or colesevelam.

In one embodiment of the invention, the compound of the formula I is administered in combination with an LDL receptor inducer (Low Density Lipoprotein; see U.S. Pat. No. 6,342,512), such as, for example, HMR1171, HMR1586 or those as described in WO2005097738.

In one embodiment of the invention, the compound of the formula 1 is administered in combination with an ABCA1 expression enhancer as are described for example in WO2006072393.

In a further embodiment of the invention, the compound of the formula I is administered in combination with an RNAi therapeutic agent which is directed against PCSK9 (Proprotein Convertase Subtilisin/Kexin type 9).

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor (acyl-CoA:cholesterol acyltransferase) such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor (adenosine triphosphate) such as, for example, SB-204990.

In one embodiment of the invention, the compound of the formula I is administered in combination with a squalene synthetase inhibitor such as, for example, BMS-188494, TAK-475 or as described in WO2005077907, JP2007022943.

In one embodiment of the invention, the compound of the formula I is administered in combination with a lipoprotein (a) antagonist such as, for example, gemcabene (CI-1027).

In one embodiment of the invention, the compound of the formula I is administered in combination with an agonist of GPR109A (HM74A receptor agonist; NAR agonist (nicotinic acid receptor agonist)), such as, for example, nicotinic acid or extended release niacin in conjunction with MK-0524A or those compounds described in WO2006045565, WO2006045564, WO2006069242, WO2006124490, WO2006113150, WO2007017261, WO2007017262, WO2007017265, WO2007015744, WO2007027532.

In another embodiment of the invention, the compound of the formula I is administered in combination with an agonist of GPR116 as are described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide, gliclazide or glimepiride.

In one embodiment, the compound of the formula I is administered in combination with a substance which enhances insulin secretion, such as, for example, KCP-265 (WO2003097064) or those described in WO2007026761.

In one embodiment, the compound of the formula I is administered in combination with agonists of the glucose-dependent insulinotropic receptor (GDIR) such as, for example, APD-668.

In one embodiment, the compound of the formula I is administered in combination with a biguanide such as, for example, metformin.

In yet another embodiment, the compound of the formula I is administered in combination with a meglitinide such as, for example, repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment, the compound of the formula I is administered in combination with glucagon receptor antagonists such as, for example, A-770077 or NNC-25-2504 or as described in WO2004100875 or WO2005065680.

In one embodiment, the compound of the formula I is administered in combination with activators of glucokinase, such as, for example, R-1511, R-1440, LY-2121260 (WO2004063179), PSN-105, PSN-110, GKA-50 or those as are described for example in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515, WO2006104030, WO2007014619.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with TNF agonists (tumor necrosis factor).

In one embodiment, the compound of the formula I is administered in combination with CRF agonists (corticotropin-releasing factor).

In one embodiment, the compound of the formula I is administered in combination with 5HT agonists (serotonin reuptake).

In one embodiment, the compound of the formula I is administered in combination with TR-β agonists (thyroid receptor).

In one embodiment, the compound of the formula I is administered in combination with inhibitors of glutamine-fructose-6-phosphate amidotransferase (GFAT), as are described for example in WO2004101528.

In one embodiment, the compound of the formula I is administered in combination with inhibitors of dipeptidylpeptidase IV (DPP-IV), such as, for example, vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200, GW-825964X, KRP-104, DP-893, ABT-341, ABT-279 or another salt thereof or those compounds as are described in WO2003074500, WO2003106456, WO2004037169, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2, DE 10 2005 012873.4, JP2006160733, WO2006071752, WO2006065826, WO2006078676, WO2006073167, WO2006068163, WO2006090915, WO2006104356, WO2006127530, WO2006111261, WO2007015767, WO2007024993, WO2007029086.

In one embodiment of the invention, the compound of the formula I is administered in combination with Janumet™, a fixed combination of sitagliptin phosphate with metformin hydrochloride.

In one embodiment, the compound of the formula I is administered in combination with inhibitors of 11-beta-hydroxysteroid dehydrogenase 1 (11β-HSDI), such as, for example, BVT-2733, JNJ-25918646, INCB-13739 or those as are described for example in WO200190090-94, WO200343999, WO2004112782, WO200344000, WO200344009, WO2004112779, WO2004113310, WO2004103980, WO2004112784, WO 2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329; WO2006066109, WO2006074244, WO2006078006, WO2006106423, WO2006132436, WO2006134481, WO2006134467, WO2006135795, WO2006136502, WO2006138695, WO2006133926, WO2007003521, WO2007007688, US2007066584, WO2007047625, WO2007051811, WO2007051810.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, PCT/EP2005/005311, PCT/EP2005/005321, PCT/EP2005/007151, DE 10 2004 060542.4, WO2007009911, WO2007028145.

In one embodiment, the compound of the formula I is administered in combination with modulators of the sodium-dependent glucose transporter 1 or 2 (SGLT1, SGLT2), such as, for example, KGA-2727, T-1095, SGL-0010, AVE 2268, SAR 7226 and sergliflozin or as are described for example in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895 or by A. L. Handlon in Expert Opin. Ther. Patents (2005) 15(11), 1531-1540.

In one embodiment, the compound of the formula I is administered in combination with modulators of GPR119b as are described for example in WO2004041274.

In one embodiment, the compound of the formula I is administered in combination with modulators of GPRI 19 as are described for example in WO2005061489 (PSN-632408), WO2004065380, WO2007003960-62 and WO2007003964.

In a further embodiment, the compound of the formula I is administered in combination with modulators of GPR120.

In one embodiment, the compound of the formula I is administered in combination with inhibitors of hormone-sensitive lipase (HSL) and/or phospholipases as described for example in WO2005073199, WO2006074957, WO2006087309, WO2006111321, WO2007042178.

In one embodiment, the compound of the formula I is administered in combination with inhibitors of acetyl-CoA carboxylase (ACC) such as, for example, those described in WO199946262, WO200372197, WO2003072197, WO2005044814, WO2005108370, JP2006131559, WO2007011809, WO2007011811, WO2007013691.

In a further embodiment, the compound of the formula I is administered in combination with modulators of xanthine oxidoreductase (XOR).

In one embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase-3 beta (GSK-3 beta), as described for example in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, the compound of the formula I is administered in combination with an inhibitor of the serum/glucocorticoid regulated kinase (SGK) as described for example in WO2006072354.

In one embodiment, the compound of the formula I is administered in combination with an agonist of the RUP3 receptor as described for example in WO2007035355.

In one embodiment, the compound of the formula I is administered in combination with an inhibitor of protein kinase C beta (PKC beta) such as, for example, ruboxistaurin.

In another embodiment, the compound of the formula I is administered in combination with an activator of the gene which codes for the ataxia telangiectasia mutated (ATM) protein kinase, such, for example, chloroquine.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553, WO2005097129.

In one embodiment, the compound of the formula I is administered in combination with modulators of the glucocorticoid receptor (GR), like those described for example in WO2005090336, WO2006071609, WO2006135826.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists (neuropeptide Y) such as, for example, naphthalene-1-sulfonic acid {4-[(4-aminoquinazolin-2-ylamino)methyl]cyclohexylmethyl}amide hydrochloride (CGP 71683A);

NPY-5 receptor antagonists such as L-152804 or like those described, for example, in WO2006001318;

NPY-4 receptor antagonists like those described for example in WO2007038942;

NPY-2 receptor antagonists like those described for example in WO2007038943;

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424, WO2006095166;

derivatives of the peptide obestatin as described in WO2006096847;

CB1R (cannabinoid receptor 1) antagonists (such as, for example, rimonabant, SR147778, SLV-319, AVE-1625, MK-0364 or salts thereof or those compounds as are described for example in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007016460, WO2007020502, WO2007026215, WO2007028849, WO2007031720, WO2007031721, WO2007036945, WO2007038045, WO2007039740, US20070015810, WO2007046548, WO2007047737);

cannabinoid receptor 1/cannabinoid receptor 2 (CBl/CB2)-modulating compounds like those described for example in WO2007001939, WO2007044215, WO2007047737;

MC4 agonists (melanocortin-4); e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO2005001921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052; orexin receptor antagonists (e.g. 1-(2-methylbenzoxazol-6-yl)-341,5]naphthyridin-4-ylurea hydrochloride (SB-334867-A) or those as are described for example in WO200196302, WO200185693, WO2004085403, WO2005075458, WO2006067224);

histamine H3 receptor agonists (e.g. 3-cyclohexyl-1-(4,4-dimethyl-1,4,6,7-tetrahydro-imidazo[4,5-c]pyridin-5-yl) propan-1-one oxalic acid salt (WO 00/63208) or those as are described in WO200064884, WO2005082893, WO2006107661, WO2007003804, WO2007016496, WO2007020213);

histamine H1/histamine H3 modulators such as, for example, betahistine or its dihydrochloride;

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor (such as, for example, 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204) or those described in JP2006111553, WO2002038543, WO2007048840-843;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid (WO 99/15525) or SR-146131 (WO 0244150) or SSR-125180) or those described in WO2005116034; serotonin reuptake inhibitors (e.g. dexfenfluramine);

mixed serotonin/dopamine reuptake inhibitors (e.g. bupropion) or fixed combinations of bupropion with naltrexone;

mixed serotoninergic and noradrenergic compounds (e.g. WO 00/71549);

5-HT receptor agonists, e.g. 1-(3-ethylbenzofuran-7-yl) piperazine oxalic acid salt (WO 01/09111);

mixed dopamine/norepinephrine/acetylcholine reuptake inhibitors (e.g. tesofensine);

5-HT2C receptor agonists (such as, for example, lorcaserine hydrochloride (APD-356) or BVT-933 or those as are described in WO200077010, WO200077001-02, WO2005019180, WO2003064423, WO200242304, WO2005035533, WO2005082859, WO2006077025, WO2006103511);

5-HT6 receptor modulators such as, for example, E-6837 or BVT-74316 or those described for example in WO2005058858, WO2007054257;

bombesin receptor agonists (BRS-3 agonists);

galanin receptor antagonists;

growth hormone (e.g. human growth hormone or AOD-9604);

growth hormone-releasing compounds tert-butyl (6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (thyrotrophin-releasing hormone, see, for example, EP 0 462 884);

uncoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (dopamine agonists; bromocriptine, doprexin);

lipase/amylase inhibitors (e.g. WO 00/40569);

inhibitors of diacylglycerol O-acyltransferases (DGATs) as described for example in BAY-74-4113 or as described for example in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538;

inhibitors of fatty acid synthase (FAS) such as, for example, C75 or those as described in WO2004005277;

inhibitors of stearoyl-CoA delta9 desaturase (SCD1) like those described for example in WO2007009236, WO2007044085, WO2007046867, WO2007046868, WO20070501124;

oxyntomodulin;

oleoyl-estrone;

or agonists or partial agonists of thyroid hormone receptor agonists such as, for example: KB-2115 or such as those described in WO20058279, WO200172692, WO200194293, WO2003084915, WO2004018421, WO2005092316, WO2007003419, WO2007009913, WO2007039125.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1.

In one embodiment of the invention, the further active ingredient is leptin;

see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the further active ingredient is a diphenylazetidinone derivative as described for example in U.S. Pat. No. 6,992,067 or U.S. Pat. No. 7,205,290.

In one embodiment, the compound of the formula I is administered in combination with bulking agents, preferably insoluble bulking agents (see, for example, Carob/CAROMAX® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with CAROMAX® is possible in one preparation or by separate administration of compounds of the formula I and CAROMAX®. CAROMAX® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

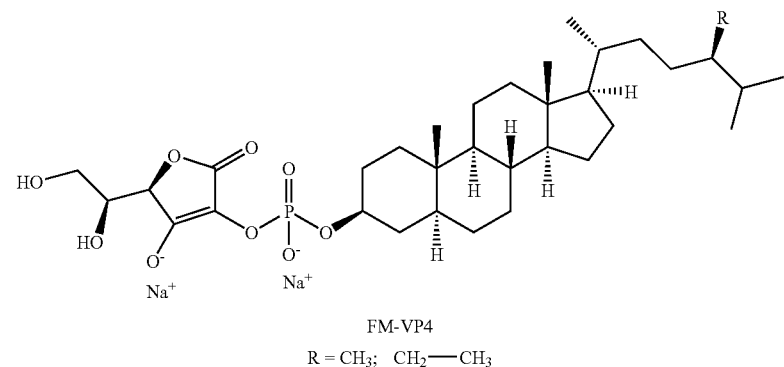

FM-VP4
R = CH₃; CH₂—CH₃

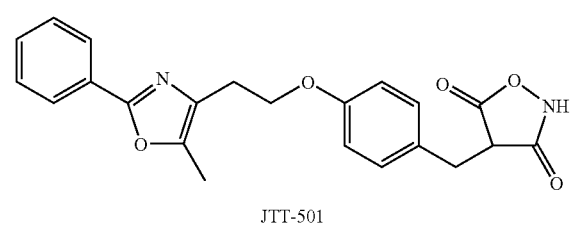

JTT-501

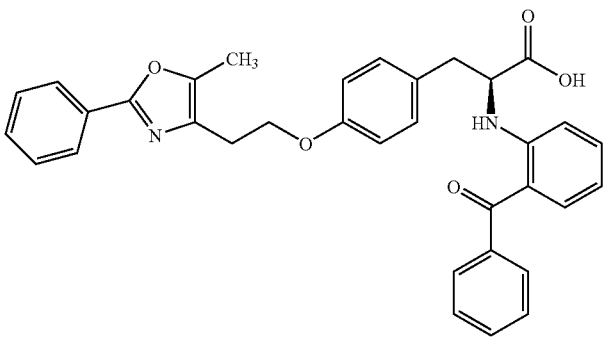

GI 262570

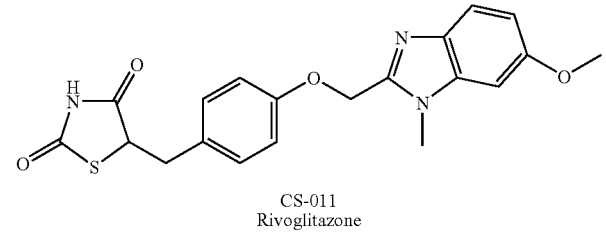

CS-011
Rivoglitazone

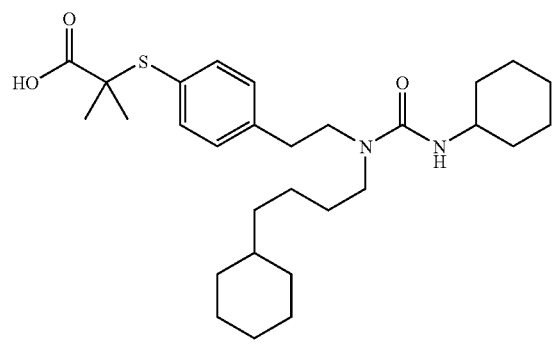

GW-9578

-continued
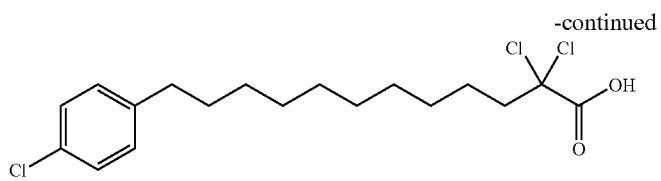
K-111
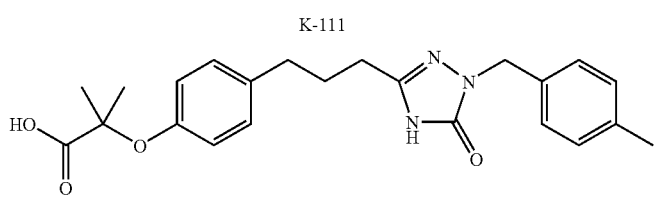
LY-674
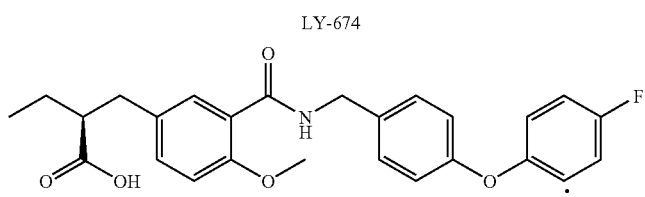
KRP-101
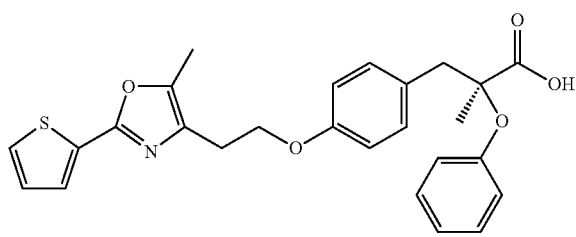
LY-510929
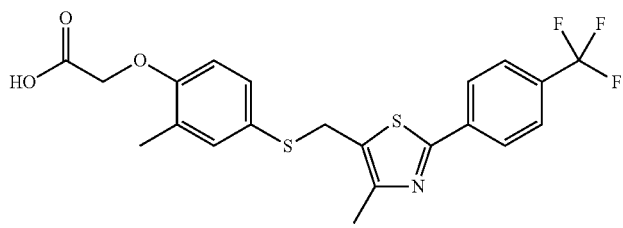
GW-501516
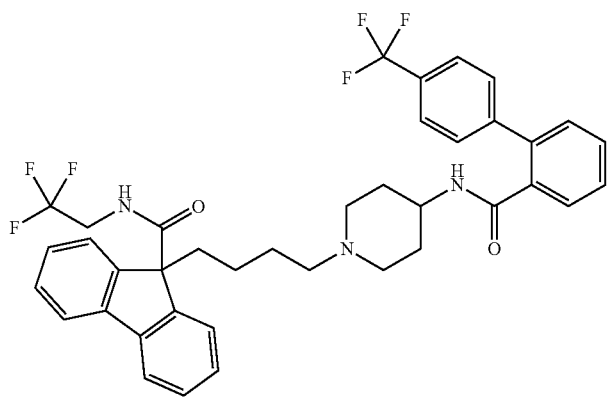
BMS-201038

-continued
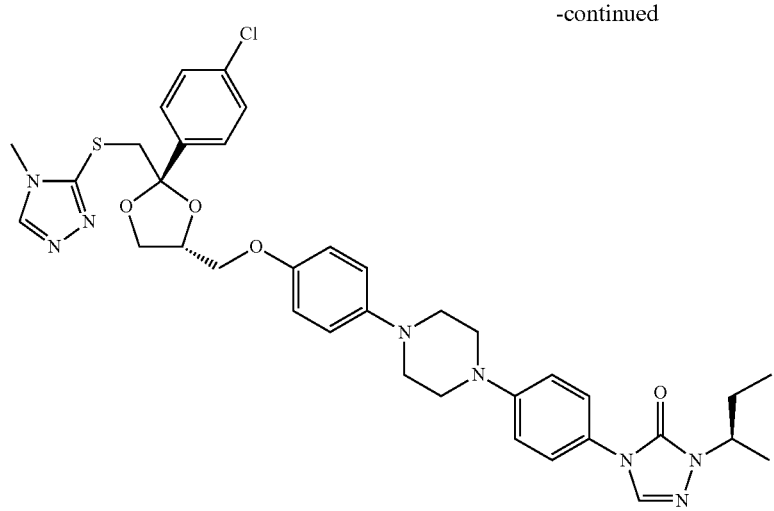
R-103757
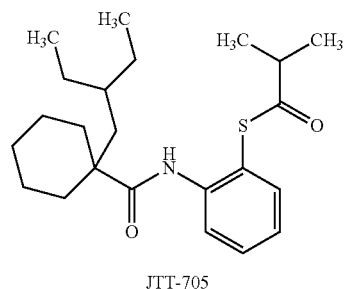
JTT-705
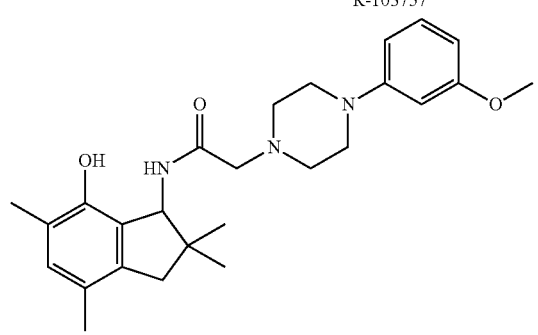
OPC-14117
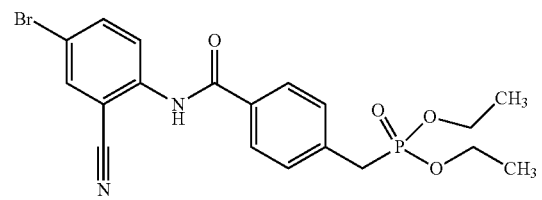
NO-1886
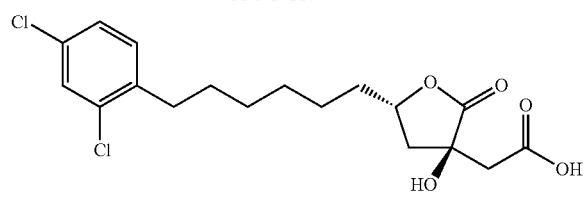
SB-204990
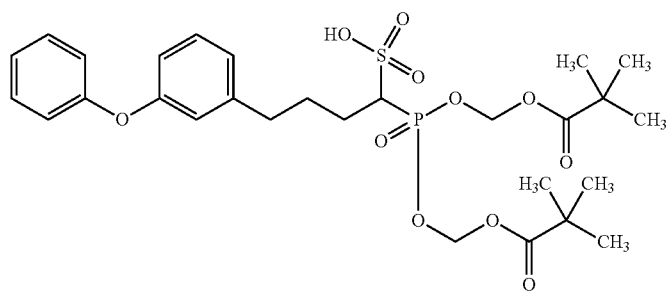
BMS-188494
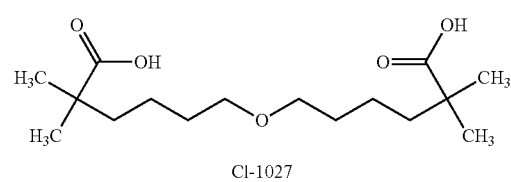
CI-1027
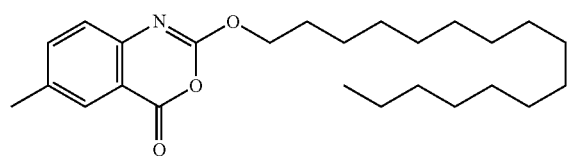
ATL-962

-continued
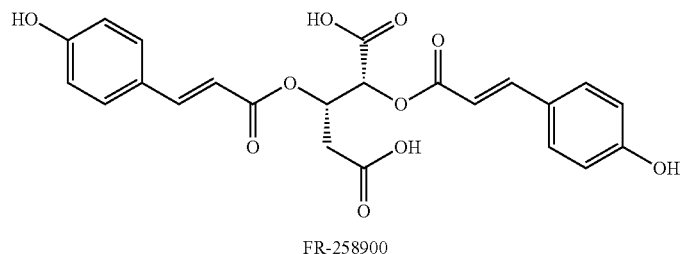
FR-258900
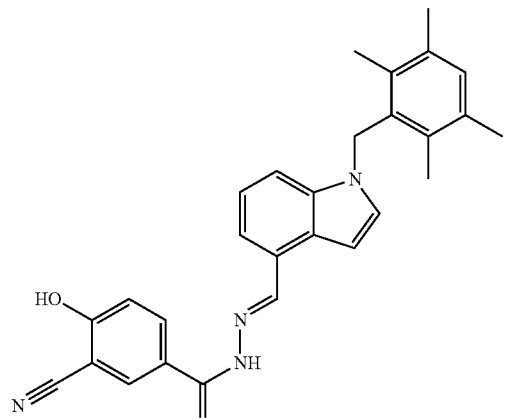
NNC-25-2504
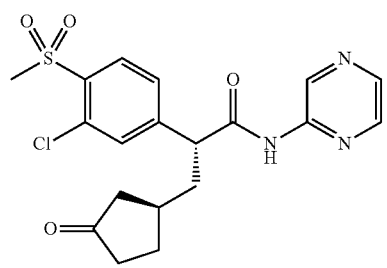
R-1440
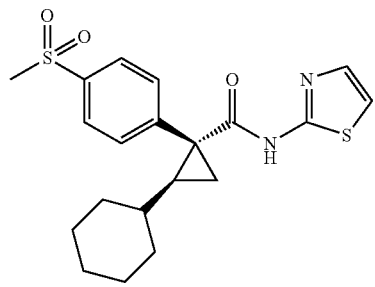
LY-2121260
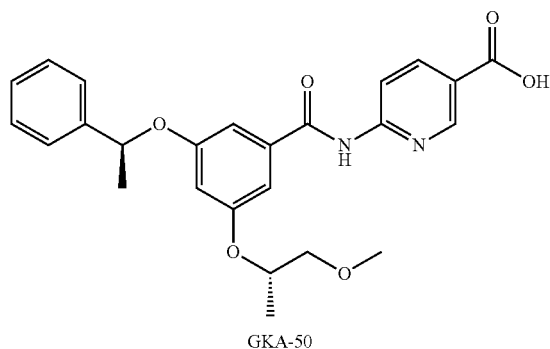
GKA-50
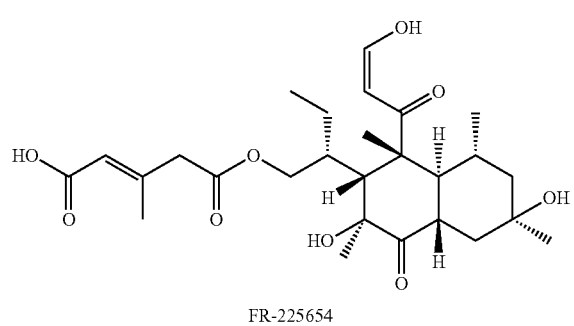
FR-225654
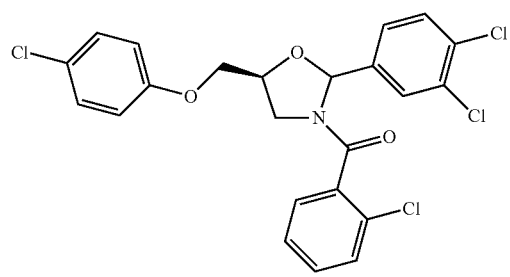
KST-48
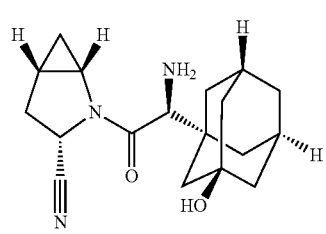
BMS-477118

23
24
-continued
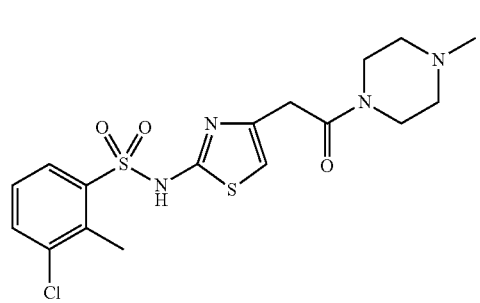
BVT-2733
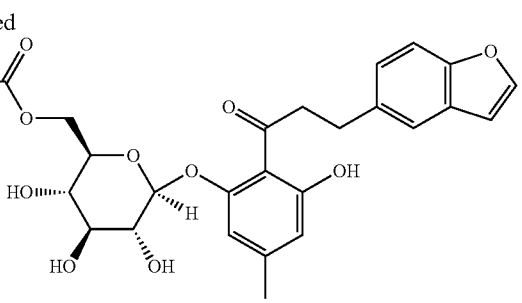
T-1095
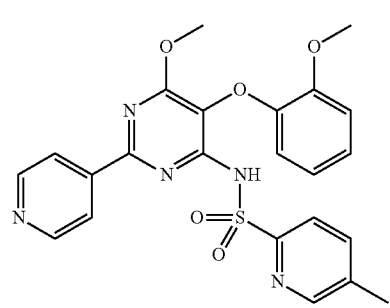
SPP-301
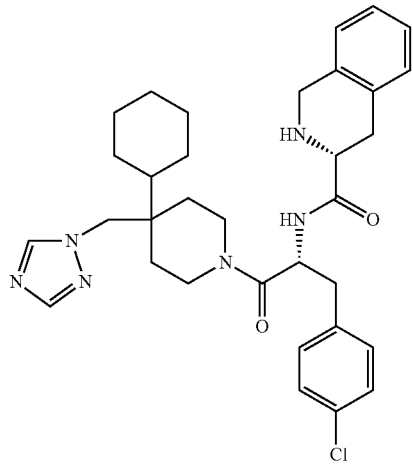
THIQ
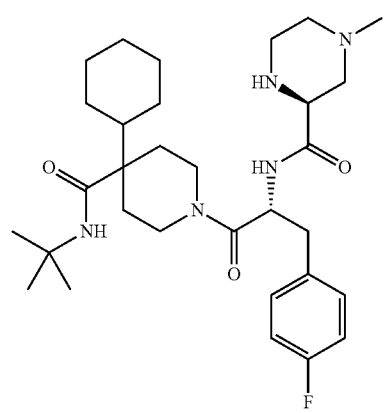
MB243
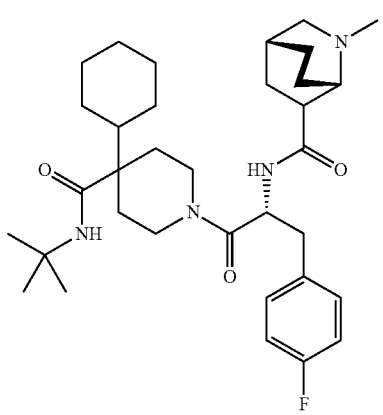
RY764
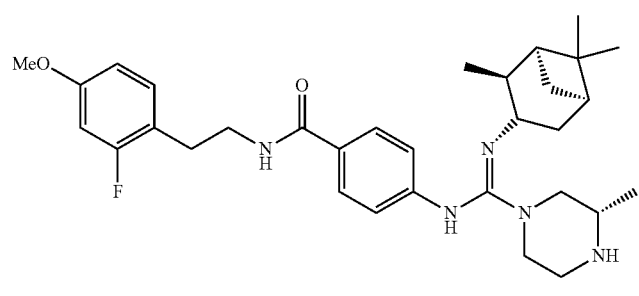
CHIR-785

-continued
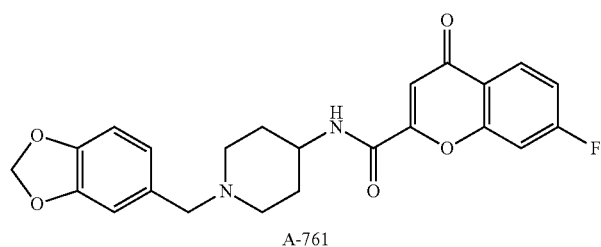
A-761
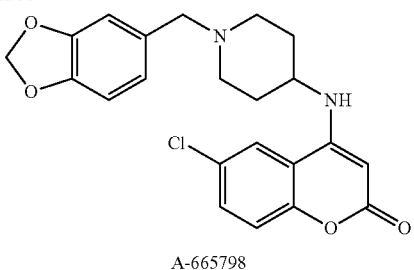
A-665798
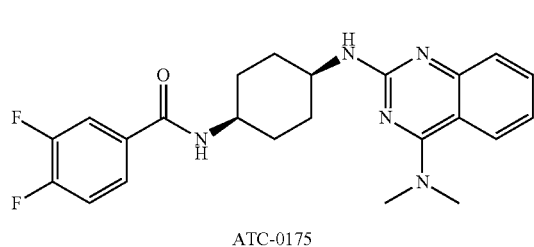
ATC-0175
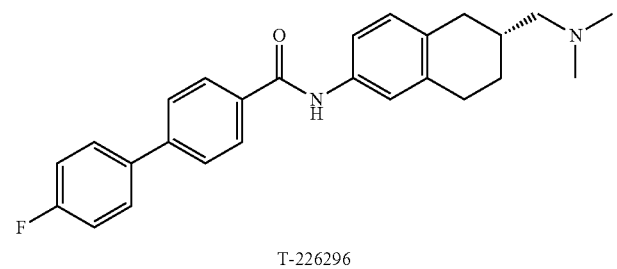
T-226296
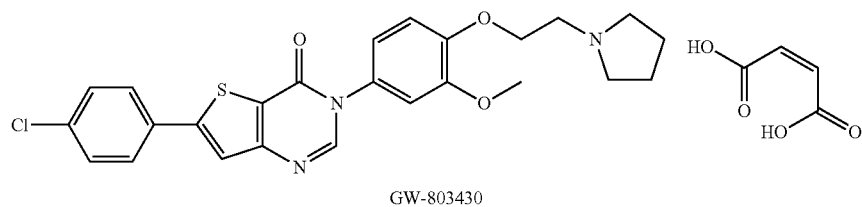
GW-803430
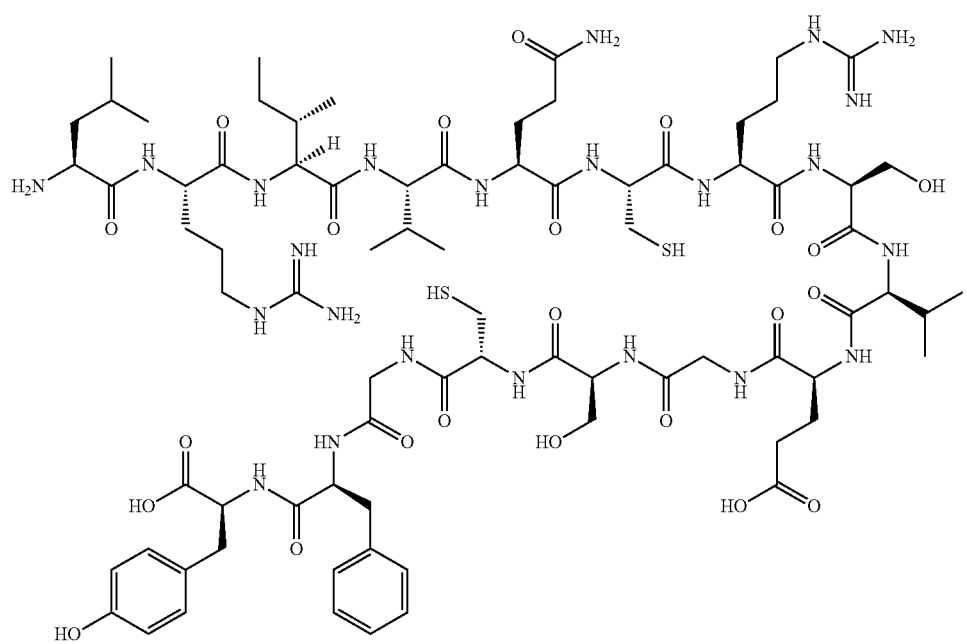
AOD-9604

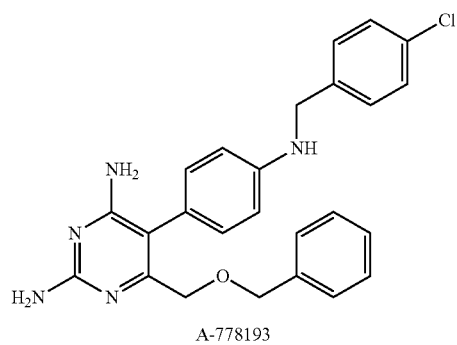
A-778193
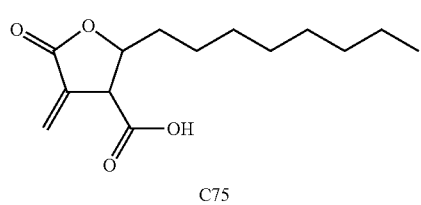
C75
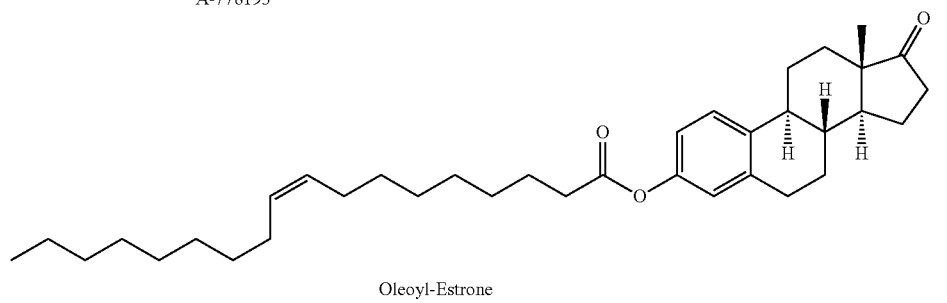
Oleoyl-Estrone
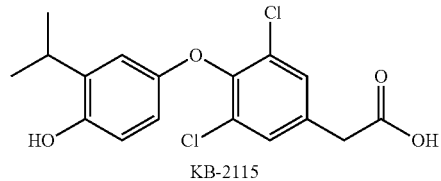
KB-2115
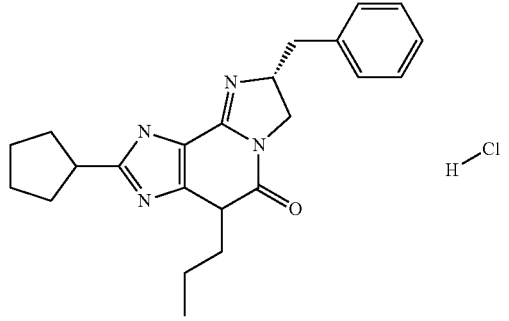
KCP-265 x HCl
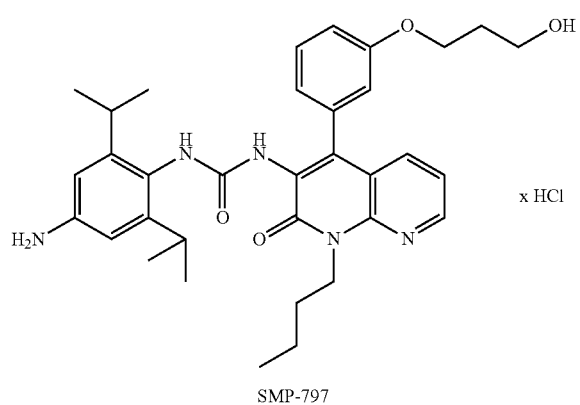
SMP-797
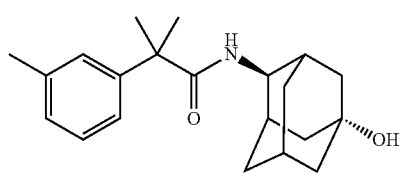
JNJ-25918646
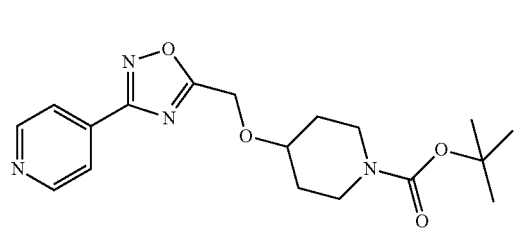
PSN-632408
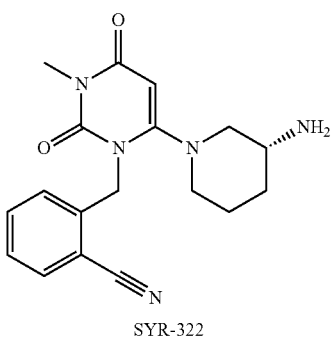
SYR-322

-continued
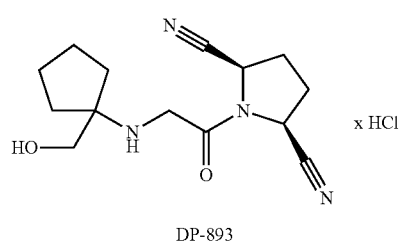
DP-893
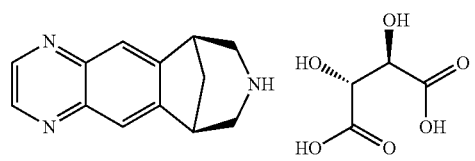
Varenicline Tartrate
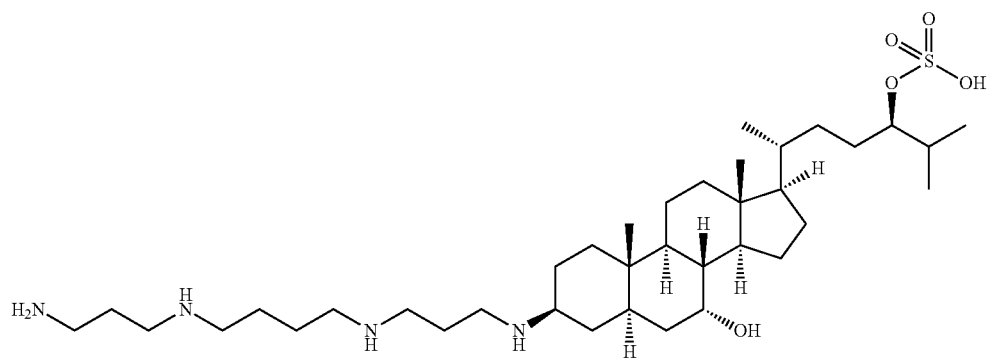
Trodusquemine
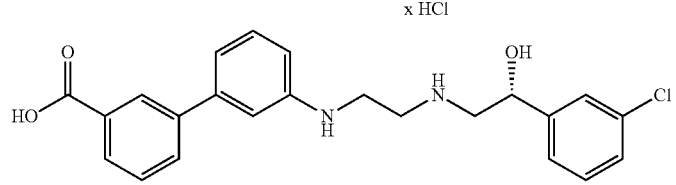
Solabegron
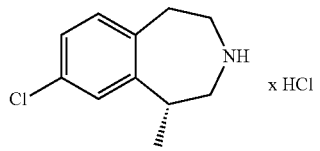
Lorcaserin Hydrochloride
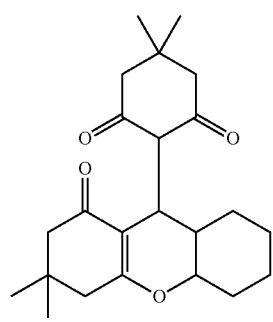
L-152804
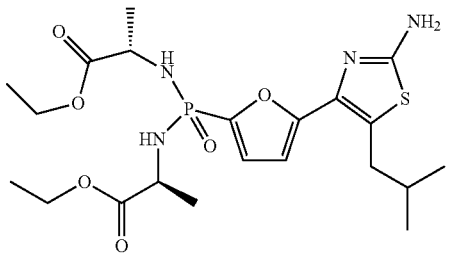
MB-06322
CS-917
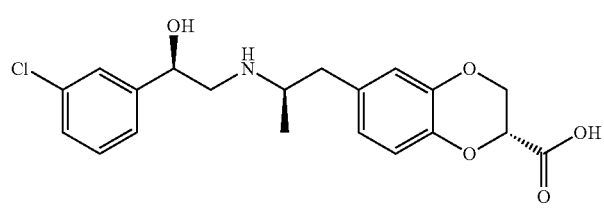
N-5984

-continued
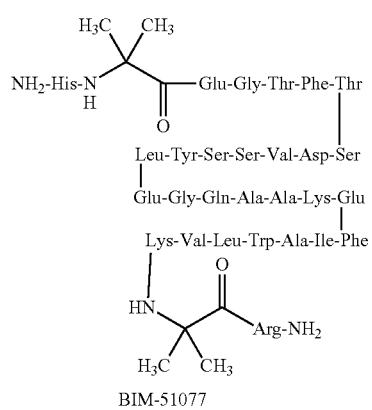
BIM-51077
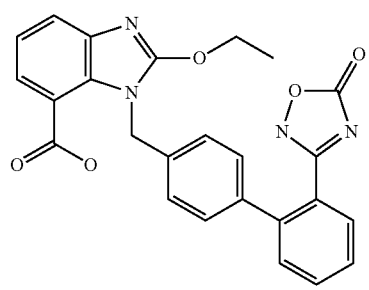
TAK-536
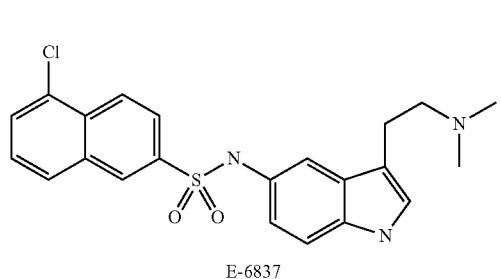
E-6837
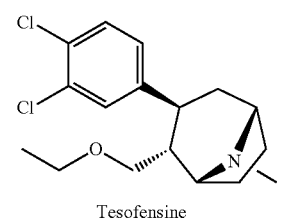
Tesofensine
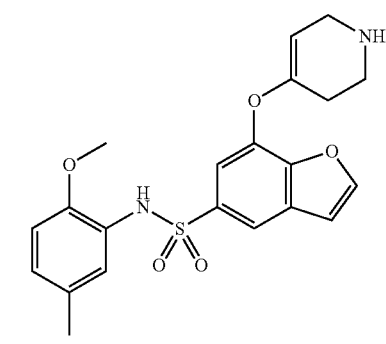
BVT-74316
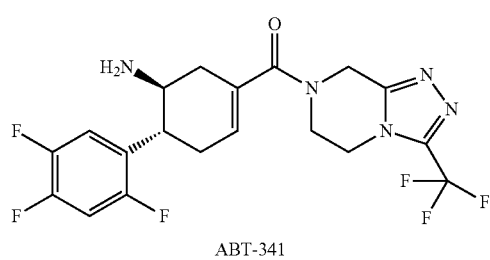
ABT-341
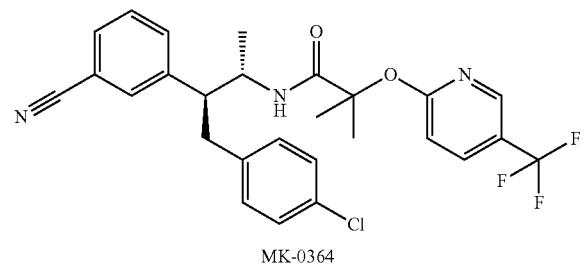
MK-0364
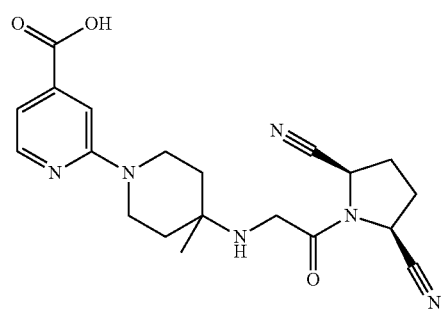
ABT-279
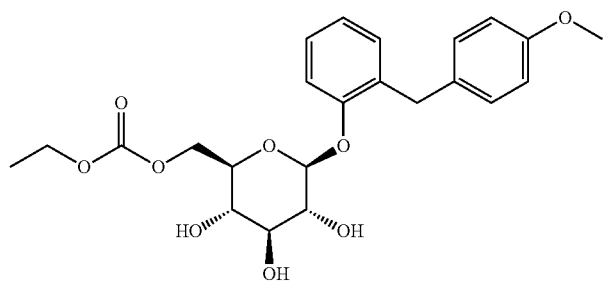
Sergliflozin -continued
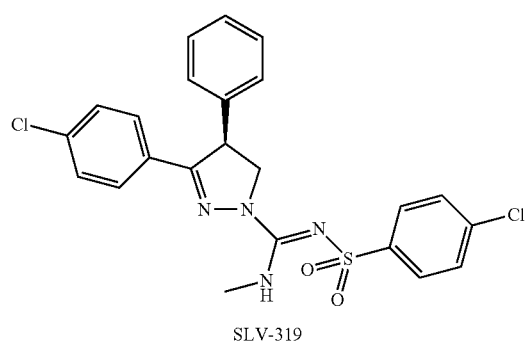
SLV-319
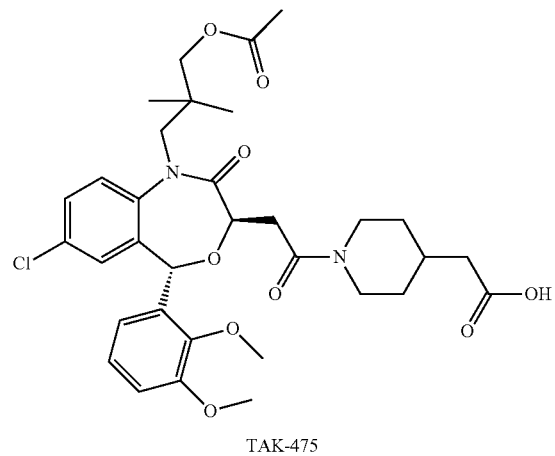
TAK-475
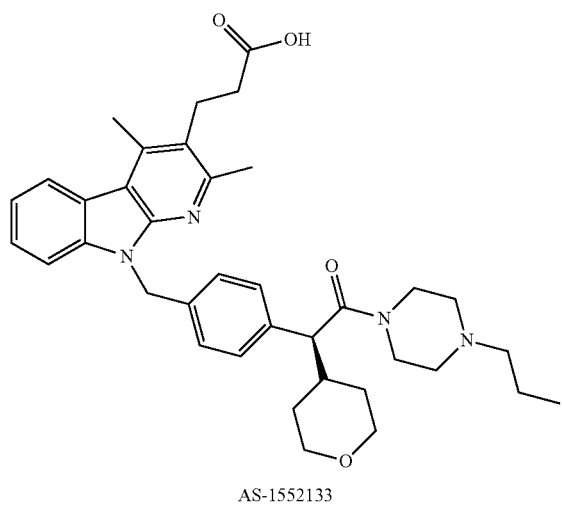
AS-1552133
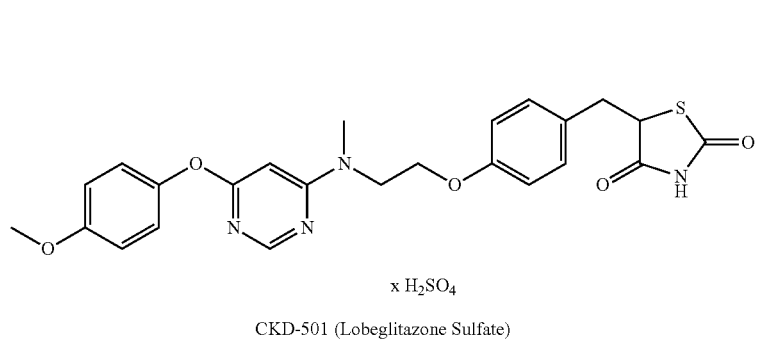
x H₂SO₄
CKD-501 (Lobeglitazone Sulfate)
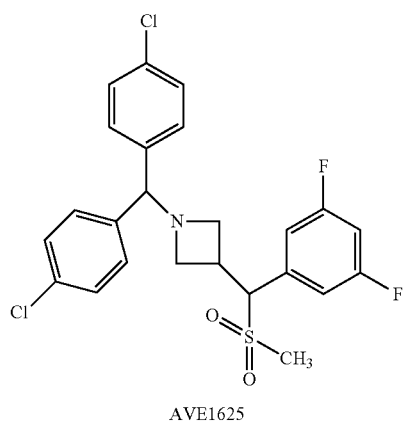
AVE1625

The examples detailed below serve to illustrate the invention without, however, restricting it.

TABLE 1

![Formula I structure]

| Ex. | R1 | R2 | R3 | R4 | R5 | R6 | m | R7 | R8 | Linkage |
|---|---|---|---|---|---|---|---|---|---|---|
| 1 | Br | H | i-Pr | H | H | — | 0 | H | H | 4 |
| 2 | CF₃ | H | Cl | H | H | — | 0 | H | H | 4 |
| 3 | Cl | Cl | H | H | H | — | 0 | H | H | 4 |
| 4 | CF₃ | H | i-Pr | H | H | — | 0 | H | H | 4 |

The activity of the compounds was tested as follows:

In-vitro FLIPR Assay with Recombinant Cells which Express the GPCR GPR40

Function-testing assays were carried out by means of the FLIPR technique ("fluorescence imaging plate reader", Molecular Devices Corp.). For this purpose, agonist-induced alterations in the intracellular concentration of $Ca^{2+}$ in recombinant HEK293 cells which express the GPCR GPR40 were determined.

For the investigations, cells were seeded in 96-well microtiter plates (60 000 cells/well) and left to grow overnight. The medium was removed and the cells were incubated in buffer which contained the fluorescent dye Fluo-4. After this loading with dye, the cells were washed, test substance was added and alterations in the intracellular $Ca^{2+}$ concentration were measured in the FLIPR instrument. Results have been depicted as percentage alteration relative to the control (0%: no test substance added; 100%: 10 µM reference agonist linoleic acid added) used to calculate dose/activity plots and $EC_{50}$ values were determined.

TABLE 2

Biological activity

| Ex. | $EC_{50}$ [µM] |
|---|---|
| 2 | 0.7 |
| 3 | 0.8 |

It is evident from the table that the compounds of the formula I activate the GPR40 receptor and thus are very suitable for the treatment of hyperglycemia and diabetes. The insulin secretion is increased by the compounds of the formula I (see Itoh et al., Nature 2003, 422, 173-176).

Owing to the activation of the GPR40 receptor, the compounds of the formula I can also be used for the treatment or prevention of further diseases.

The compounds of the present invention are particularly suitable for the treatment and/or prevention of:

1. -disorders of fatty acid metabolism and glucose utilization disorders
   disorders in which insulin resistance is involved
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic B cells
   prevention of macro
   and microvascular disorders
3. Various other conditions which may be associated with the metabolic syndrome or syndrome X, such as:
   increased abdominal girth
   dyslipidemia (e.g. hypertriglyceridemia and/or low HDL)
   insulin resistance
   hypercoagulability
   hyperuricemia
   microalbuminemia
   thromboses, hypercoagulable and prothrombotic states (arterial and venous)
   high blood pressure
   heart failure such as, for example (but not restricted thereto), following myocardial infarction, hypertensive heart disease or cardiomyopathy
4. Memory impairments, intellectual deficits, CNS disorders such as
   dementia in the elderly
   Alzheimer's disease
   treatment of diminished attention or vigilance
   schizophrenia The compounds of the formula I can be prepared for example by converting suitable starting materials of the formula II

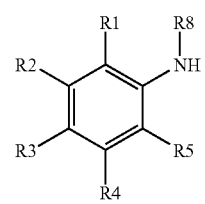

with oxalyl chloride into the oxamoyl chlorides of the formula III

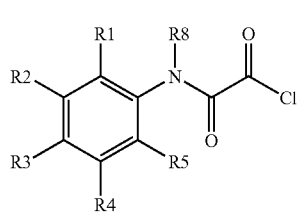

in suitable solvents such as, for example, ethyl acetate or acetonitrile. The compounds of the formula III prepared in this way are reacted with aminophenyl-substituted carboxylic acids of the formula IV

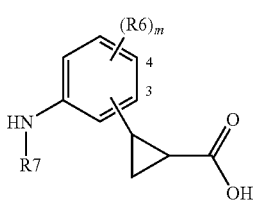

in suitable solvents such as, for example, acetonitrile, 1,2-dichloroethane or dichloromethane at suitable temperatures, preferably at the boiling point, to give compounds of the formula I.

The general preparation of the examples is described in detail below:

Experimental Section:

General Experimental Procedure:

Preparation of the Oxamoyl Chloride:

50 mg of an aniline are dissolved in 3 ml of dichloroethane and mixed with 38 µl of oxalyl chloride. The reaction solution is stirred at 100° C. for 16 hours and then concentrated.

Preparation of the Oxamides of the Formula I:

The aminophenyl-substituted cyclopropylcarboxylic acid is added to a suspension of the oxamoyl chloride in 3 ml of acetonitrile and stirred at 90° C. for 15 hours. The resulting precipitate is filtered off with suction and, if necessary, purified by flash chromatography (SiO$_2$, dichlormethane-isopropanol).

The compounds were analyzed by LC/MS. The appropriate molecular peak (M+H)+ was detectable by LC/MS for all examples.

We claim:

1. A compound of formula I

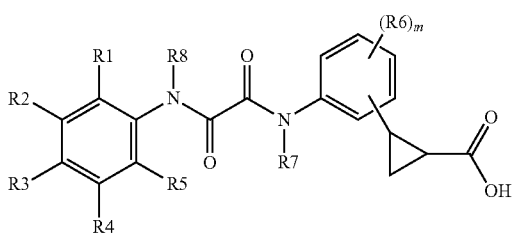

wherein:

R1, R2, R3, R4 and R5 are, independently, H, F, Cl, Br, CN, CF$_3$, OH, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, O-Bn, SO$_2$—(C$_1$-C$_4$)-alkyl, SO$_3$H, SO$_2$NR9R10, NR9R10 or SO$_2$—N-piperidinyl, wherein the alkyl and phenyl are optionally substituted one or more times by R12;

R7 and R8 are, independently, H or (C$_1$-C$_6$)-alkyl;

m is 0, 1, 2, 3 or 4;

R6 is OH, F, Cl, Br, CN, OCH$_3$, OCF$_3$, CH$_3$, CF$_3$, (C$_1$-C$_6$)-alkyl or O—(C$_1$-C$_6$)-alkyl, wherein the alkyl is optionally substituted one or more times by OH, F, Cl, Br or CN;

R9 and R10 are, independently, H, (C$_1$-C$_6$)-alkyl or phenyl, wherein the alkyl is optionally substituted one or more times by F, Cl or Br, and the phenyl is optionally substituted one or more times by R6;

R11 is F, Cl, Br, CN, OH, O—(C$_1$-C$_6$)-alkyl, (C$_1$-C$_6$)-alkyl, (C$_2$-C$_6$)-alkenyl, (C$_2$-C$_6$)-alkynyl or NR9R10; and R12 is F, Cl, Br, CN, OH, O—(C$_1$-C$_6$)-alkyl, (C$_1$-C$_6$)-alkyl, (C$_2$-C$_6$)-alkenyl, (C$_2$-C$_6$)-alkynyl, NR9R10, COOH, COO—(C$_1$-C$_4$)-alkyl, SCH$_3$, SCF$_3$, SO$_2$—(C$_1$-C$_4$)-alkyl, SO$_3$H or SO$_2$NR9R10;

or a pharmaceutically acceptable salt thereof.

2. The compound according to claim 1, wherein

R7 and R8 are H;

or a pharmaceutically acceptable salt thereof.

3. The compound according to claim 1, wherein

R1 is H, F, Cl, Br, CN, CF$_3$, OH, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, or O-Bn;

R2 is H, F, Cl, Br, CN, CF$_3$, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, or O-Bn;

R3 is H, F, Cl, Br, CN, CF$_3$, OH, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, or O-Bn;

R4 is H, F, Cl, Br, CN, CF$_3$, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, or O-Bn;

R5 is H, F, Cl, Br, CN, CF$_3$, OH, OCF$_3$, OCHF$_2$, SCH$_3$, SCF$_3$, phenyl, O-phenyl, COOH, COO—(C$_1$-C$_6$)-alkyl, CO—(C$_1$-C$_6$)-alkyl, (C$_1$-C$_6$)-alkyl, O—(C$_1$-C$_6$)-alkyl, O-Bn;

provided that at least one of the radicals R1 to R5 is not hydrogen;

m is 0; and

R9 and R10 are, independently, H or (C$_1$-C$_6$)-alkyl, wherein the alkyl is optionally substituted one or more times by F, Cl or Br;

or a pharmaceutically acceptable salt thereof.

4. A pharmaceutical composition comprising the compound according to claim 1 or a pharmaceutically acceptable salt thereof, in combination with a pharmacologically acceptable carrier or excipient.

5. A pharmaceutical composition comprising the compound according to claim 2 or a pharmaceutically acceptable salt thereof, in combination with a pharmacologically acceptable carrier or excipient.

6. A pharmaceutical composition comprising the compound according to claim 3 or a pharmaceutically acceptable salt thereof, in combination with a pharmacologically acceptable carrier or excipient.

7. The pharmaceutical composition according to claim 4, further comprising one additional active ingredient.

8. The pharmaceutical composition according to claim 7, wherein the additional active ingredient is selected from the group consisting of antidiabetics, hypoglycemic active ingredients, HMGCoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, MTP inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose-1,6-bisphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, melanocyte-stimulating hormone agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, lipase/amylase inhibitors, PPAR modulators, RXR modulators, TR-β agonists and amphetamines.

9. A method for lowering blood glucose, for treating diabetes or for increasing insulin secretion, in a patient in need thereof, comprising administering to the patient a pharmaceutically effective amount of the compound according to claim 1 or a pharmaceutically acceptable salt thereof.

10. A method for lowering blood glucose, for treating diabetes or for increasing insulin secretion, in a patient in need thereof, comprising administering to the patient a pharmaceutically effective amount of the compound according to claim 2 or a pharmaceutically acceptable salt thereof.

11. A method for lowering blood glucose, for treating diabetes or for increasing insulin secretion, in a patient in need thereof, comprising administering to the patient a pharmaceutically effective amount of the compound according to claim 3 or a pharmaceutically acceptable salt thereof.

12. A process for producing a pharmaceutical composition comprising the compound according to claim 1 or a pharmaceutically acceptable thereof, in combination with a pharmacologically acceptable carrier or excipient, comprising mixing the compound according to claim 1 or the pharmaceutically acceptable salt thereof with the pharmacologically acceptable carrier or excipient, and converting this mixture into a form suitable for administration.

* * * * *